United States Patent [19]
Kashuba et al.

[11] Patent Number: 5,098,437
[45] Date of Patent: Mar. 24, 1992

[54] ACETABULAR CUP POSITIONING INSERT

[75] Inventors: Glen A. Kashuba, Lyndhurst; Jon I. Klippel, Flemington, both of N.J.

[73] Assignee: Pfizer Hospital Products Group, Inc., New York, N.Y.

[21] Appl. No.: 661,157

[22] Filed: Feb. 13, 1991

[51] Int. Cl.$^5$ ............................ A61F 5/04; A61F 2/36
[52] U.S. Cl. ........................................ 606/89; 606/91; 606/99; 623/23
[58] Field of Search .................. 606/86, 91, 99, 89, 606/81; 623/16, 18-23, 17

[56] References Cited

U.S. PATENT DOCUMENTS

| | | | |
|---|---|---|---|
| 3,859,992 | 1/1975 | Amstutz | 606/91 |
| 4,135,517 | 1/1979 | Reale | 606/89 |
| 4,528,980 | 7/1985 | Kenna | 606/80 |
| 4,563,778 | 1/1986 | Roche | 623/18 |
| 4,632,111 | 12/1986 | Roche | 606/53 |
| 4,678,472 | 7/1987 | Noiles | 623/18 |
| 4,770,661 | 9/1988 | Oh | 623/18 |
| 4,801,301 | 1/1989 | Noiles | 623/18 |
| 4,978,356 | 12/1990 | Noiles | 623/18 |

Primary Examiner—Mickey Yu
Assistant Examiner—Michael Brown
Attorney, Agent, or Firm—Peter C. Richardson; Lawrence C. Akers; Raymond W. Augustin

[57] ABSTRACT

An acetabular cup for use as a prosthetic implant has an insert with a body including a central bore for receiving a positioning rod therein. A key element is formed on the bore and is adapted to align the positioning rod. The insert has a locating element formed on an outer surface of the body and also includes spring elements extending radially outwardly from the body. The acetabular cup has a generally hemispherical shell member coupled to the outer surface of the insert. The shell has an outer surface for engaging the acetabulum and an inner surface having a circumferential groove for receiving the spring elements. The spring elements may be deflected radially inwardly out of engagement with the groove for releasing the insert from the shell. The shell has a plurality of apertures extending from its inner to its outer surface, which apertures are located in an asymmetrical pattern about the shell. The shell includes a recess on its open end for receiving the locating element on the insert to align the insert at a predetermined orientation with respect to the apertures in the shell. The engagement of the insert onto the shell and the engagement of the locating element in the recess aligns the key element on the central bore and, therefore, the positioning rod at a predetermined orientation with respect to the apertures in the shell.

20 Claims, 8 Drawing Sheets

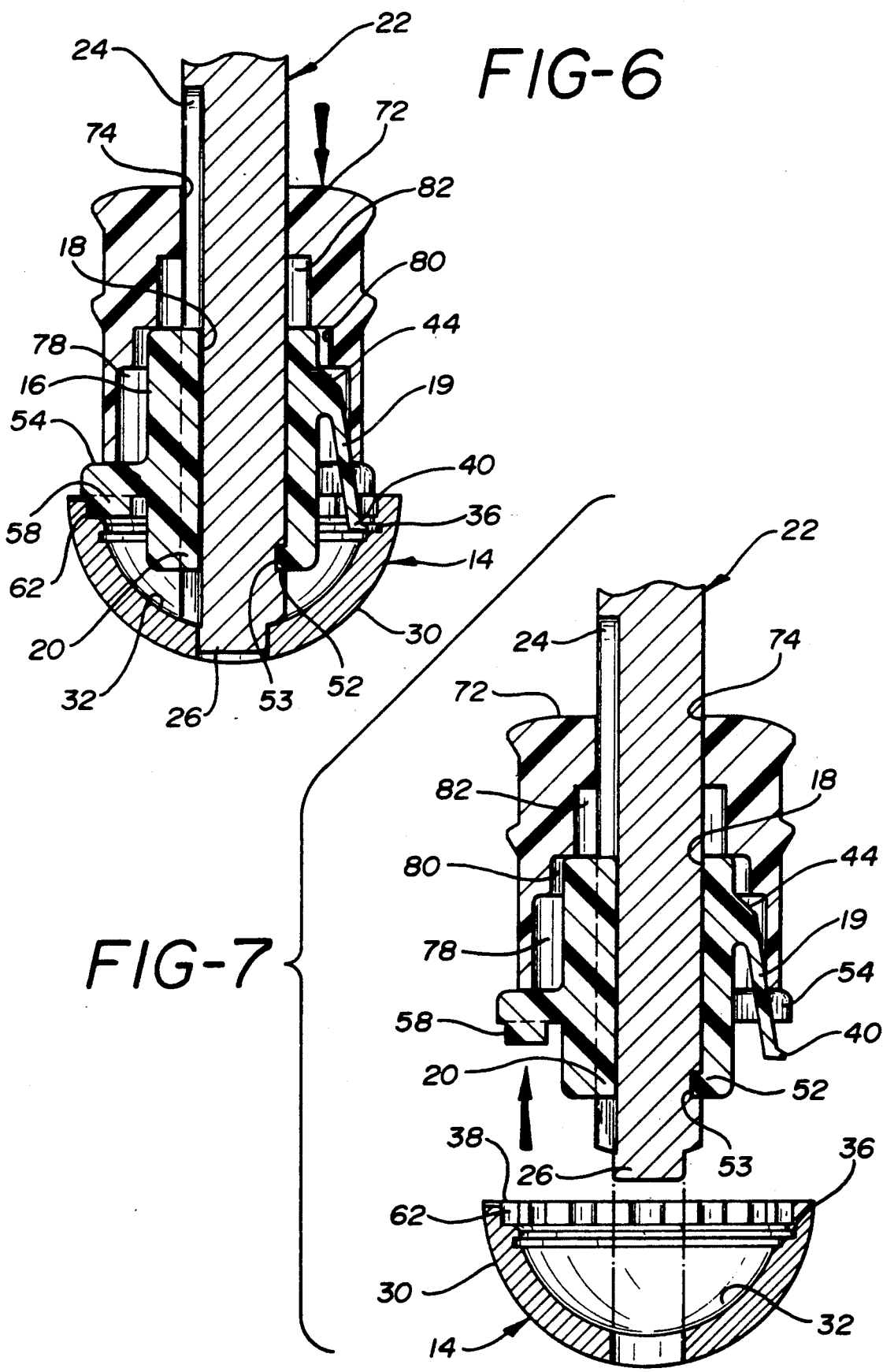

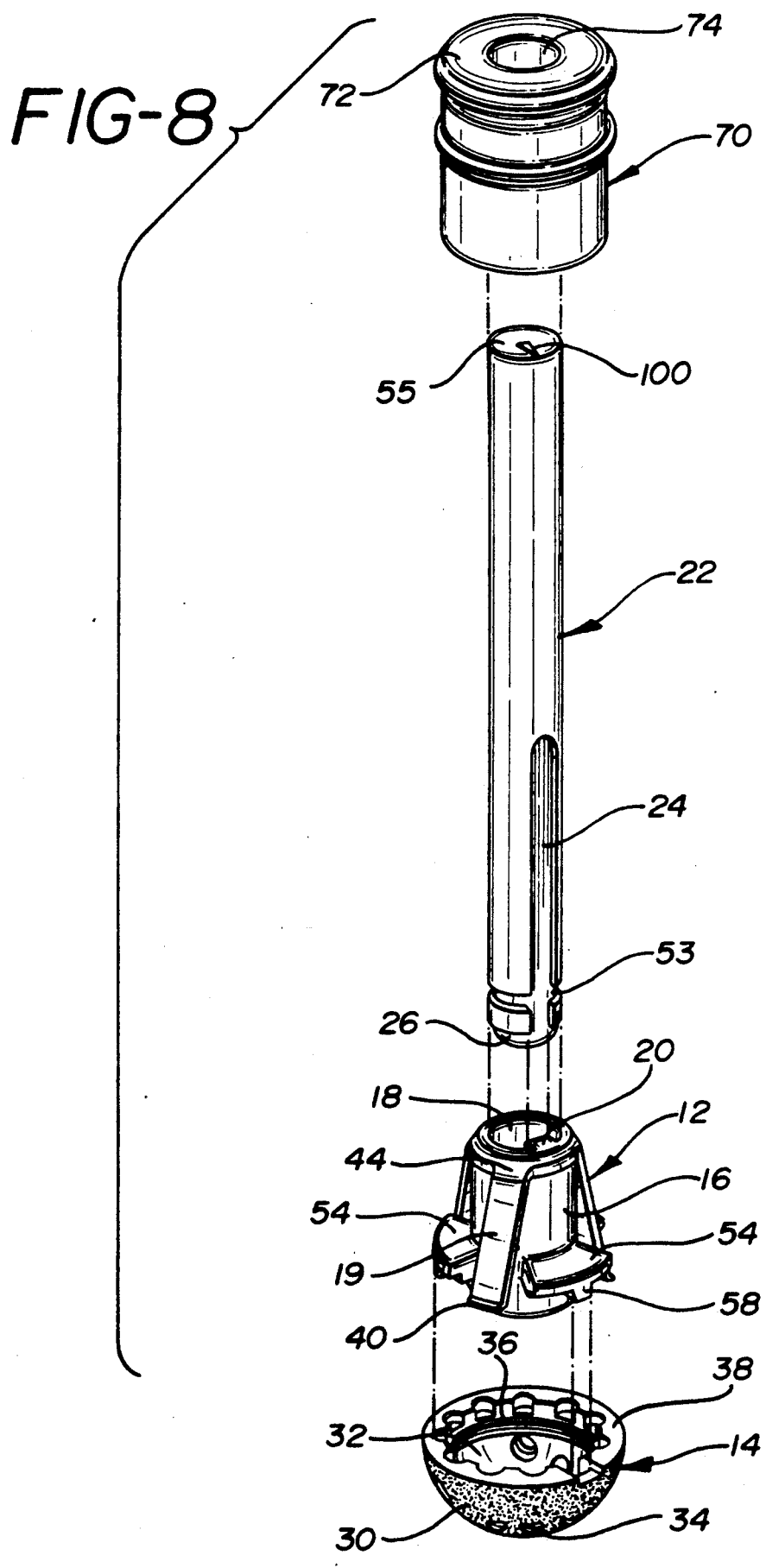

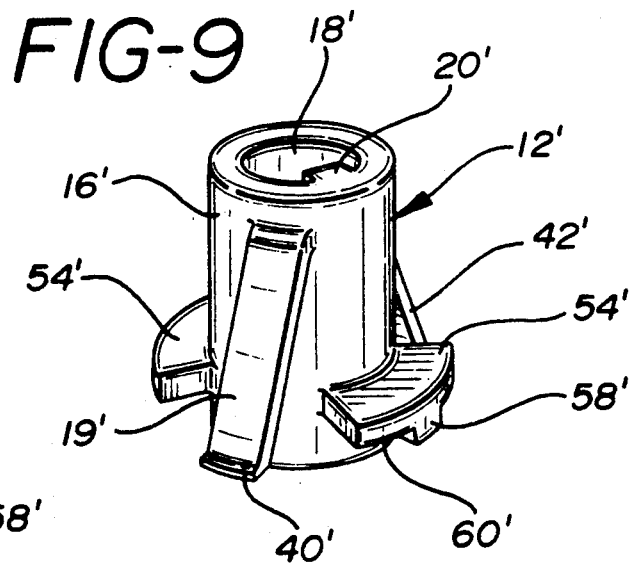
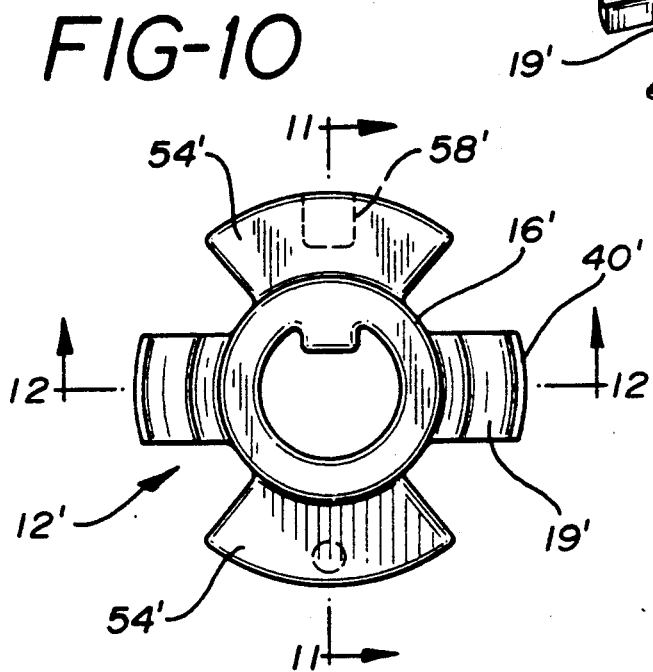
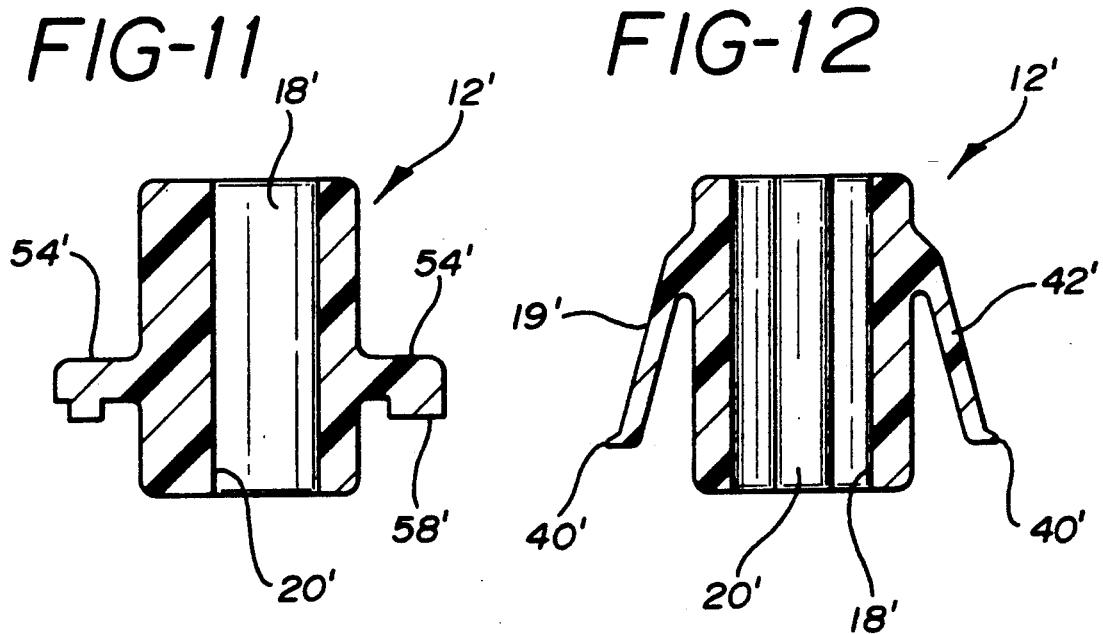

ACETABULAR CUP POSITIONING INSERT

BACKGROUND OF THE INVENTION

1. Field of the Invention

This invention relates to apparatus for positioning a prosthetic acetabular cup within an acetabulum during total hip replacement surgery.

2. Description of the Prior Art

As part of total hip replacement surgery, a prosthetic acetabular cup is implanted within the human acetabulum to substitute for the socket of the human hip joint. This is usually done to compensate for severe damage of the acetabulum due to disease, trauma, or other factors. A prosthetic femoral component is mated with the acetabular cup component to complete the total hip replacement surgery. In order to achieve optimal performance of the combined acetabular and femoral prostheses, the acetabular cup must be properly positioned in the acetabulum. An improperly positioned acetabular component can lead to dislocations of the hip joint, decreased range of motion, and eventual loosening or failure of both the acetabular and femoral components.

Interoperative placement of the acetabular component can be a surgically demanding task. The orthopedic surgeon must adequately fix the cup in the proper alignment while hampered by limited surgical exposure and relatively few clear reference points. In the past, the acetabular cup was provided in the form of an outer shell preassembled to a polyethylene bearing insert. Alternately, the cup shell and the bearing insert were provided as separate pieces to be assembled after the shell is affixed via bone screws or other means.

A wide variety of instruments are known in the art for inserting acetabular cup implants into position in the acetabulum. Many such insertion instruments include a first handle with a second handle extending therefrom to assist in the insertion procedure. Typically, the second handle is in a fixed orientation relative to the first handle. Examples of such acetabular instruments are disclosed in U.S. Pat. Nos. 4,528,980 to Kenna, 4,475,549 to Oh, 4,305,394 to Bertuch, Jr., 3,859,992 to Amstutz and 4,632,111 to Roche. Once the acetabular cup is attached to such instruments, the handles are in a fixed orientation with regard to the cup. With certain cup designs a particular orientation of the cup may be desirable to achieve proper anatomic positioning. An example of such a cup design is a cup which has pegs protruding from the outer surface, such as the pegged cup disclosed in U.S. Pat. No. 3,781,918 to Mathys. Accordingly, when the first and second handles are both in a permanently fixed orientation with regard to the cup, it may result in the second handle being in an awkward or inconvenient position in order to insert the cup in the desired orientation. Also, if the first handle needs to be rotated about its axis during the insertion of the cup or the removal of the insertion instrument from the cup, a fixed secondary handle may be awkward or get in the way.

Traditional cup positioners generally include at least a pusher ball sized and shaped to fit the recess within the acetabular component, a positioner arm, a positioner flange juxtaposed the pusher ball, and a pusher arm connected to the ball and to the flange to enable the user to push the prosthetic acetabular cup, when resting on the flange, into the prepared acetabulum. Generally, the cup must be manually held against the flange during implantation. In some cases, the cup is aligned on the flange by means of small projecting pins which can engage complementary holes in the face of the cup.

Separate cup pushers are often used in conjunction with a cup positioner to address some of these problems. The positioner is removed once the cup has been placed in the acetabulum, and the pusher is separately used to apply pressure to the cup.

In addition to the pusher ball, the flange, and the pusher arm, some acetabular cup positioning instruments include means for establishing reference angles to better insure proper alignment of the prosthetic cup. Many traditional positioner designs include a reference arm for establishing the abduction angle. U.S. Pat. No. 4,475,549 further includes means for establishing the anteversion angle.

The acetabular cup shell of the present invention has a shell with apertures for receiving bone screws and is usually not provided preassembled to a polyethylene bearing insert. The shell aperture pattern is asymmetrical with more holes being located in the superior quadrant of the shell than in the inferior quadrant (when placed in the acetabulum). As indicated above, the accurate positioning and orientation of the replacement shell is crucial for the restoration of adequate biomechanics during a total hip replacement procedure. For assuring this orientation, the implantation device is required to provide approximately 45° abduction and 20° anteversion, while firmly gripping the acetabular cup shell component during impaction and the subsequent release of the shell following final positioning. In the case of the present invention, the rod-like positioning instrument must also orient the superior hemisphere of the shell to the superior hemisphere of the acetabulum, assuring the accuracy of strategically placed screw holes which target adequate body masses of the anatomy and avoid the violation of critical vascular structures.

In the present invention, the positioning procedure just described is performed with the use of the molded, disposable plastic insert of the present invention which is coupled to each shell component at a specific orientation to the superiorly oriented aperture pattern thereon. The insert is adapted to receive a positioning rod in a manner specifically referencing the superior oriented screw hole pattern. The plastic insert can be engaged by the positioning rod only in an orientation consistent with the shell's superior screw hole pattern. This orientation is obtained by a central key or keyway on the rod's tip which is aligned with the rod's known alignment guide provisions (abduction/anteversion). The key or keyway engages a mating key element on the insert. Following positioning, impaction, and stability check, the rod/ plastic insert combination is removed from the shell by depressing the resilient spring or spring-like elements which disengage the undercut or groove of the shell component. The shell, being left intact, is now ready for continuation of the necessary procedure including screw application and bearing insert assembly. The retracted rod/plastic insert combination is then removed from the surgical site and the plastic insert of the present invention can be disengaged from the rod and disposed of.

The insert brings both simplicity and cost efficiency to modern total hip arthroplasty. By simply releasing the resilient spring elements, an efficient means of shell positioning and impaction is provided without the use of a bulky, multi-part positioning system commonly found in most hospitals. For hospital economics, extensive and costly instrumentation systems can be eliminated from increasingly tightened budgets. Both inexperienced and experienced support staffs are able to easily adapt to the simplified surgical procedure.

SUMMARY OF THE INVENTION

It is an object of the invention to provide a preassembled insert and acetabular cup shell which facilitates the mating of various size acetabular cups with a standard positioning instrument at a desired orientation.

It is a further object of this invention to provide an inexpensive insert which can releasably engage a prosthetic acetabular cup, to be used during implantation, and then be discarded after the acetabular cup shell has been implanted within the acetabulum.

It is yet another object of the invention to provide an insert for an acetabular cup shell which is simple to manufacture, simple in design, but can withstand the force required for impaction into an acetabulum during implantation.

These and other objects of the invention are accomplished by an insert for a prosthetic acetabular cup of the type having a generally hemispherical shape with an open end and a recessed groove or undercut formed on an inner surface thereof adjacent the open end. The insert includes a body having a central bore therethrough. The bore includes a key element formed thereon for aligning a positioning instrument utilized during implantation of the acetabular cup.

The insert body has a first end adapted to be received within the acetabular cup shell and a second end extending outwardly of the open end of the shell. A spring element is connected to the insert body at the first end thereof and has a free end spaced radially outwardly of the second end of the body. The free end of the spring element has a flange for engaging the recessed groove on the inner surface of the acetabular cup shell for retaining the insert within the cup.

The insert also includes an alignment element formed on an outer surface of its body for engaging the acetabular cup shell at a predetermined position thereon. The free end of the spring element is radially spaced from the body a distance sufficient to permit the flexion of the spring element towards the body which disengages the flange from the recess on the inner surface of the acetabular cup shell.

The recess on the shell is in the form of a circumferential groove extending around the inner surface of the shell adjacent the open end thereof. A groove of this type is utilized in many acetabular cup systems to hold a polyethylene bearing insert in a "snap-fit" engagement with the outer shell. The polyethylene bearing insert is adapted to receive the spherical head of a prosthetic hip implant. It is intended that the insert for the prosthetic acetabular cup shell disclosed herein is to be removed after implantation of the shell so that the standard bearing insert may be inserted into the shell and support of the hip prosthesis after implantation.

The alignment element insert of the present invention is in the form of a key located on an outer surface of the body which key engages a recess on the acetabular cup shell. The apertures in the acetabular cup shell are asymmetric with the alignment recess which recess is positioned at a predetermined point around the circumference of the inner surface of the shell. Thus upon engagement of the key formed on the insert body with the corresponding alignment recess on the acetabular cup shell inner surface, the key element formed on the inner bore of the insert body is aligned at a desired orientation with respect to the aperture pattern of the prosthetic acetabular cup shell. The key element on the central bore of the insert engages a corresponding keyway on the positioning rod so that upon engagement the rod is positioned with respect to the insert and therefore with respect to the aperture pattern in the shell. This allows the surgeon to position the apertures in a correct position vis a vis the bony portion of the pelvis so that insertion of bone screws through the shell apertures contacts cortical bone in desired areas.

The spring element on the insert body of the present invention is integrally molded therewith from resilient plastic and includes a flange extending radially outwardly from the free end of the spring element for engaging the groove in the inner surface of the acetabular shell. The insert of the present invention is inserted within the acetabular cup by deforming the spring element radially inwardly until the flange can engage the circumferential groove at which time the developed spring forces are released, causing the spring element to move radially outwardly. This causes the flange to engage the groove thereby locking the insert within the acetabular cup shell.

Removal of the insert from the shell is accomplished by deflecting the spring element on the insert body radially inwardly, thereby disengaging the flange from the circumferential groove on the shell and allowing the axial movement of the insert out of the open end of the acetabular cup shell. This removal is usually performed with the positioning rod coupled to the insert. If removal of the rod attached to the insert is desired, the insert body of the present invention may include a spring element adjacent the bore which engages a complimentary recess in the positioning rod for locking the insert on the positioning rod and preventing axial movement thereon.

This may be accomplished by having a circumferential groove formed at the leading end of the positioning rod which engages a second spring element formed on the insert body, which in turn engages the groove on the rod to thereby lock the positioning rod within the insert body. Again, the second spring element is deformable out of engagement with the groove on the positioning rod so that, if desired, the insert may be slid axially thereon out of engagement with the acetabular cup.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 6 is a cross-sectional view of the lower end of the assembly of FIG. 1 with the releasing cup engaging in the spring elements of the insert body;

FIG. 7 is an exploded view of the insert of the present invention being removed from the acetabular cup shell;

FIG. 8 is an exploded view of the acetabular cup positioning system including the insert of the present invention;

FIG. 9 is an isometric view of a first embodiment of the positioning insert of the present invention;

FIG. 10 is a bottom view of the insert shown in FIG. 9;

FIG. 11 is a cross-sectional view of bearing insert shown in FIG. 10 along lines 11—11;

FIG. 12 is a cross-sectional view of the bearing insert shown in FIG. 10 along lines 12—12;

DESCRIPTION OF THE PREFERRED EMBODIMENTS

Figure 1:
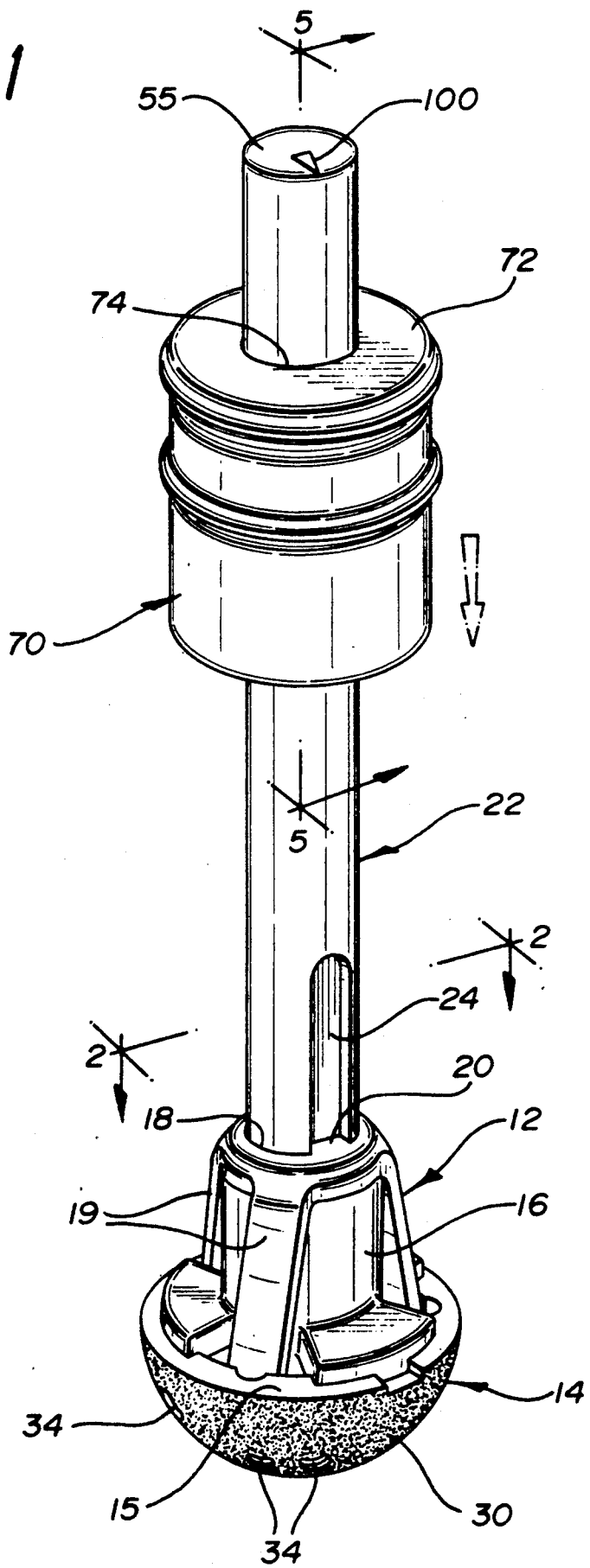
FIG. 1 is an isometric view of the insert and acetabular cup shell of the present invention mounted on a positioning rod with a release cup positioned thereon.
Figure 2:
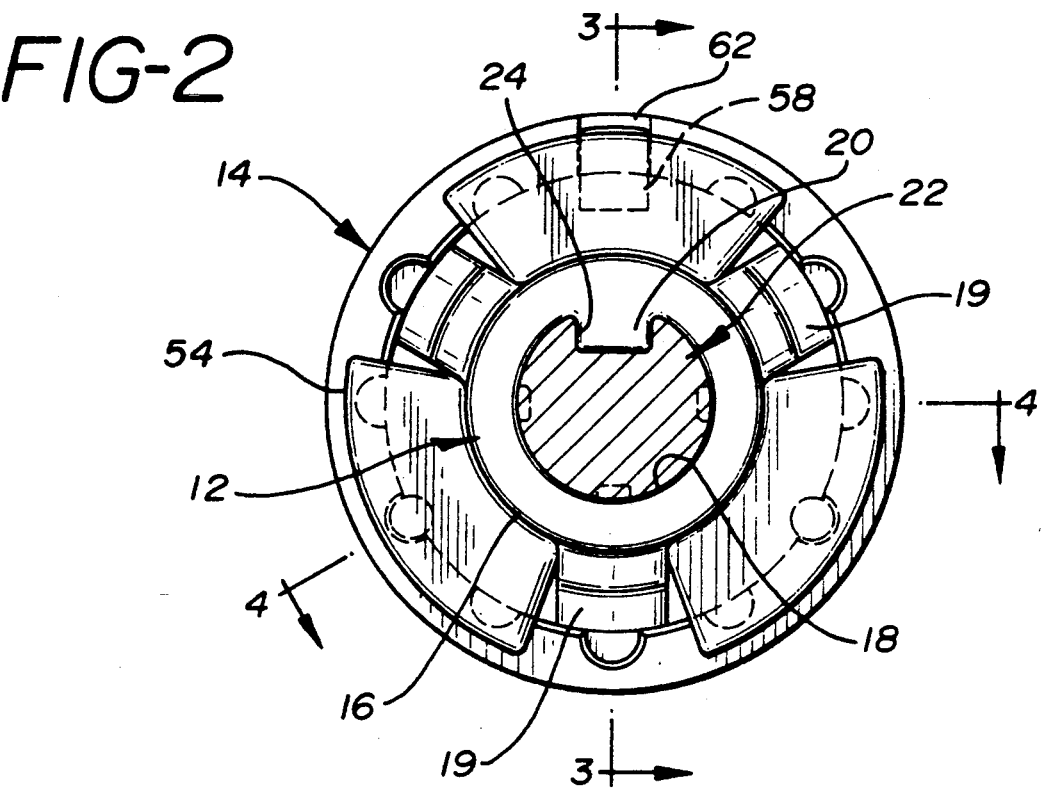
FIG. 2 is a cross-sectional view of the assembly of FIG. 1 along lines 2—2.
Figure 3:
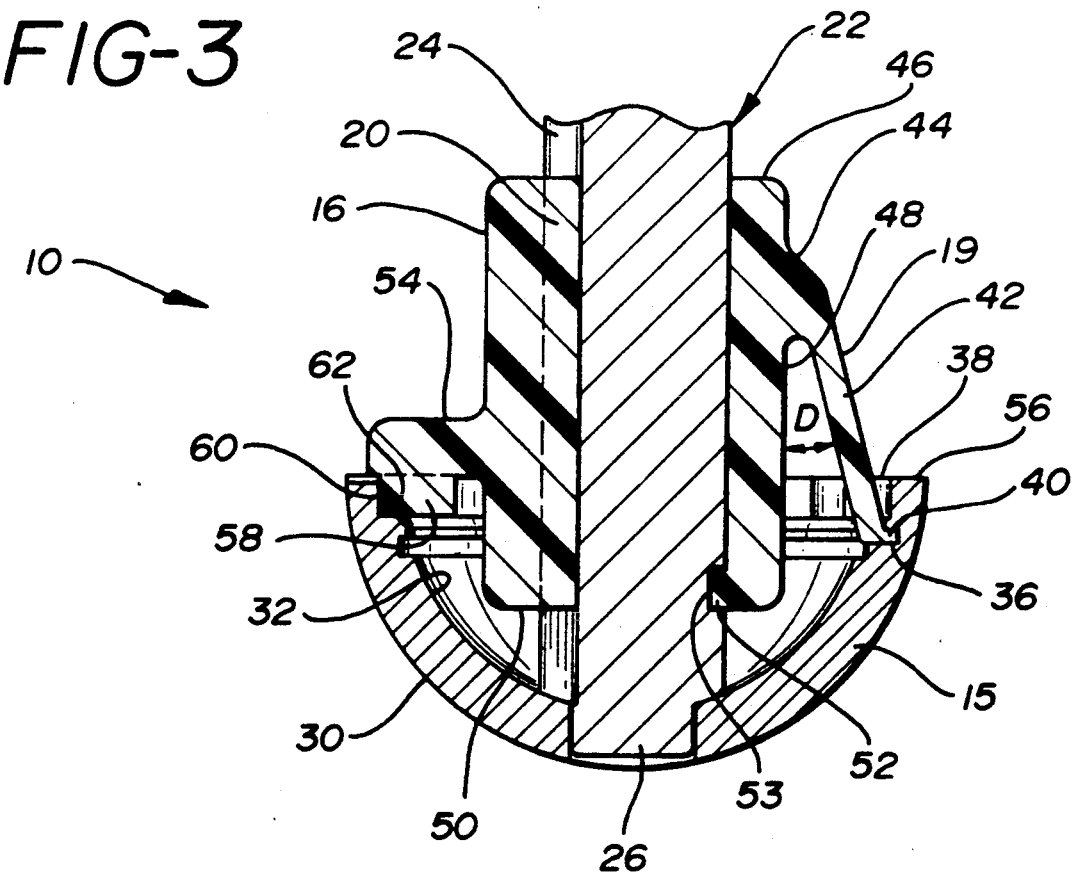
FIG. 3 is a cross-sectional view of the assembly shown in FIG. 2 along lines 3—3.
Figure 4:
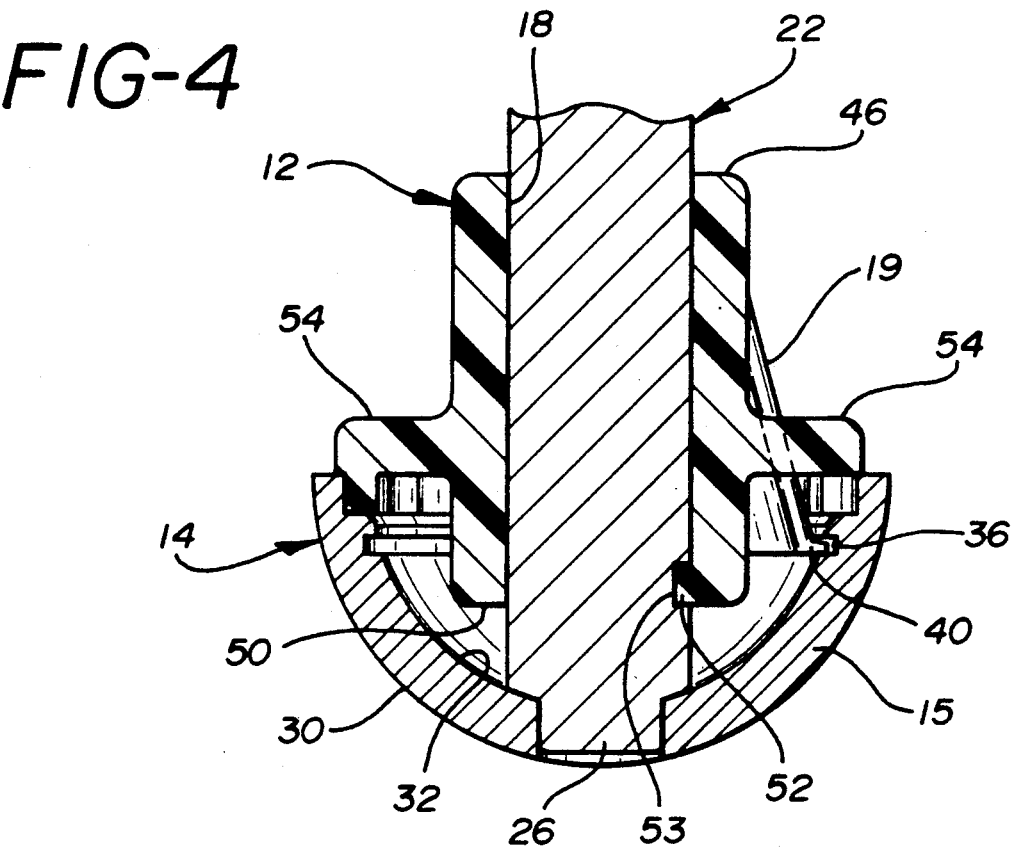
FIG. 4 is a cross-sectional view of the assembly shown in FIG. 2 along lines 4—4.
Figure 5:
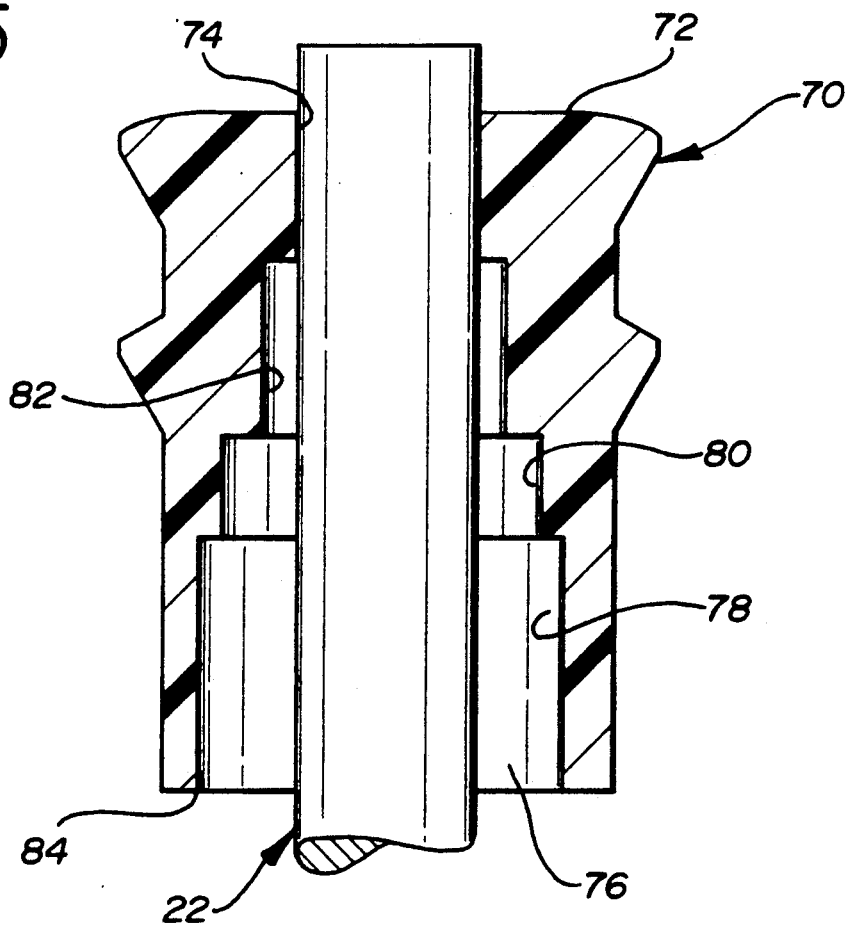
FIG. 5 is a cross-sectional view of the assembly shown in FIG. 1 along lines 5—5.

Referring to FIGS. 1-3, there is shown the acetabular cup assembly of the present invention generally denoted as 10. The assembly is composed of an insert 12 and a prosthetic acetabular cup 14. Positioning insert 12 has a body member 16 which includes a central longitudinal bore 18 and one or more spring elements 19. Circular bore 18 includes a male key element 20 extending radially into bore 18. In the preferred embodiment key element 20 extends longitudinally along the bore 18 throughout the axial extent thereof.

In the preferred embodiment a positioning rod 22 has a diameter adapted to be slidably received within bore 18 of insert 12. Positioning rod 22 includes a keyway 24 sized to engage key element 20 so that the leading end 26 of rod 22 can only be inserted into bore 18 in a specific orientation with respect thereto.

Acetabular cup 14 has a generally hemispherical shaped shell 15 with an outer surface 30, an inner surface 32, and a plurality of apertures 34 extending through the wall defined by inner and outer surfaces 32, 30. Apertures 34 are located at specific sectors of hemispherical shell 15 and are asymmetrically distributed thereon in a manner to be positioned over areas of thick cortical pelvic bone when positioned in the acetabulum (not shown) at a predetermined orientation with respect thereto. Thus bone screws (not shown) can be extended through apertures 34 to secure shell 12 to the bone.

Shell 15 has an undercut or recess 36 formed in the inner shell thereof adjacent open end 38 thereof. In the preferred embodiment recess 36 is in the form of a circumferential groove extending around the inner surface 32 of cup 14. Groove 36 is adapted to receive a flange 40 formed at the free end of spring element 19 of insert body 16. In the preferred embodiment spring element 19 is integrally molded with body 16 at an end thereof extending axially outwardly of the open end 38 of acetabular cup 14 when the insert is positioned therein. Spring element 19 is in the form of a spring element which is sprung outwardly of body 16 and thus must be inwardly deformed in order to fit within open end 38 of acetabular cup 14 and engage recess 36 formed thereon.

In the preferred embodiment, body 16 includes three spring elements 19 spaced equally distant around the circumference thereof, however, fewer or more spring elements 19 may be utilized to secure insert body 16 to acetabular cup 14. Furthermore, it is conceivable that other releasable or resilient elements may be used for coupling insert 12 to acetabular cup 14. For example, an element in the form of a spring-loaded ball radially oriented within a bore within insert body 16, capable of engaging a recess formed on the inner surface 32 of acetabular cup 14 could be used. However, it has been found that a very inexpensive way to form insert 12 is by injection molding in which plastic, such as a polyamide thermoplastic, may be used to form both body 16 and spring element 19 in a one-step operation. A nylon type 6/6 with glass filler to increase strength has been found to be a suitable plastic. This inexpensive method of manufacturing insert 12 permits it to be disposed of after a single use.

In the preferred embodiment element 19 is coupled to insert body 16 at shoulder 44 which is formed adjacent outer end 46 of insert body 16. Prior to insertion of insert 12 within acetabular cup 14, flange 40 at the free end of element 19 is sprung outwardly a distance greater than the diameter of inner surface 32 at open end 38 of acetabular cup 14. Element 19 is spaced a sufficient distance D from the outer surface 48 of insert body 16 so that spring element 19 may be deformed inwardly a sufficient distance to be inserted into open end 38 and then allowed to spring outwardly so that flange 40 engages groove 36. Likewise, when it is intended to remove positioning rod 22 with insert 12 coupled thereto from acetabular cup 14, spring arm 19 may be deformed inwardly so that flange 40 moves out of engagement with recess 36, thereby permitting the uncoupling of the shell 15 and insert 12.

Referring to FIGS. 3 and 8, in the preferred embodiment leading end 50 of insert 16 includes a resilient element 52 which may be deformed radially outwardly upon insertion of positioning rod 22 within bore 18 and then deformed inwardly to engage a groove 53 formed adjacent leading end 26 of positioning rod 22, thereby locking the positioning rod onto the insert.

In the preferred embodiment insert 12 includes at least two plates 54 which extend radially outwardly from body 16 to overlie rim 56 which surrounds open end 38 of acetabular cup 14. A key element 58 is formed on one of the plates 54 and extends outwardly of a side 60 thereof, which contacts rim 56 of acetabular cup 14 upon engagement of flange 40 with recess 36. Key element 58 is received within a recess 62 on shell 15 to position insert 12 at a specific orientation with respect to the circumference of shell 14 and therefore the pattern of apertures 34 thereon. Thus it can be seen that in its assembled condition, both the insert 12 and rod 22 can be oriented only in one position with respect to the pattern of apertures 34 on shell 15 to produce the aforementioned desired orientation of shell 15 for being connected to the acetabulum via bone screws.

In the preferred embodiment a release cup 70 is provided and includes a first end 72 including a circular opening 74 therein which is sized to slidably receive positioning rod 22. Cup 70 has a stepped bore 76 with a first larger diameter 78 and two smaller diameters 80 and 82 respectively. Bores 78, 80 have diameters complimentary to those of insert 16 so that bore 80 may receive end 46 of insert 16, and bore 78 has a diameter adapted to receive shoulder 44 of insert 12 and an upper part of spring element 19. When cup 70 is slid onto rod 22 towards end 26 thereof, corner 84 at the end of bore 78 engages the radially outer surface of spring element 19, thereby deforming the element inwardly and thereby moving flange 40 out of engagement with groove 36 to provide a simple means of releasing the positioning rod insert combination from acetabular cup 14.

Referring to FIGS. 9-12, there is shown an alternate embodiment of the insert of the present invention generally denoted as 12' which is almost identical to insert 12 described above with the exception that insert 12' includes only two spring elements 19' and two plate members 54'. As with the insert body 16 described above, insert body 16' includes a bore 18' having a key element 20' extending radially inwardly thereof and a key element 58' extending from an underside 60' of one of the plates 54'. In all respects, insert 12' functions identically to insert 12 described above.

Referring to FIG. 8, there is shown an exploded view of the release cup 72, positioning rod 22, insert 12 and acetabular cup 14 of the present invention. Normally, insert 12 comes preassembled to acetabular cup 14 so that on implantation the preassembled acetabular cup and insert are removed from a sterile package, positioning rod 22 is then inserted within bore 18 of insert 12 and locked therein via spring element 52 and groove 53, placing an orientation arrow 100 or a second handle (not shown) at a desired orientation with respect to the pattern of the apertures 34 in acetabular cup 14. After positioning the cup 14 in the acetabulum, which positioning may require the cup to be hammered via tapping end 55 of positioning rod 22 with a hammer, cup 72 is slid axially downwardly in the orientation shown in FIG. 8 to disengage the insert 12 and rod 22 assembly from acetabular cup 14. As is well known, a polyethylene bearing insert (not shown) may be inserted into the acetabular cup 14 in a "snap-fit" fashion utilizing recess 36, usually in the form of a circumferential groove.

Figure 13:
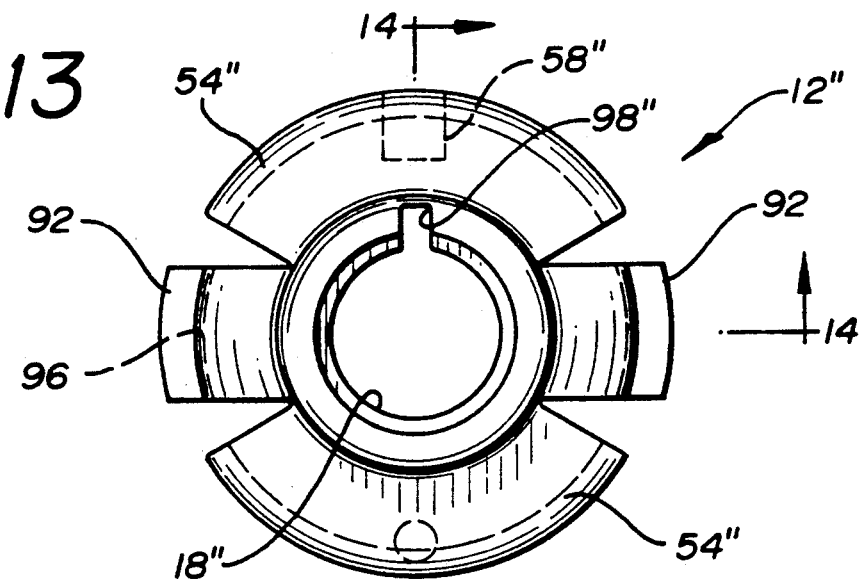
FIG. 13 is a bottom view of an alternate insert.
Figure 14:
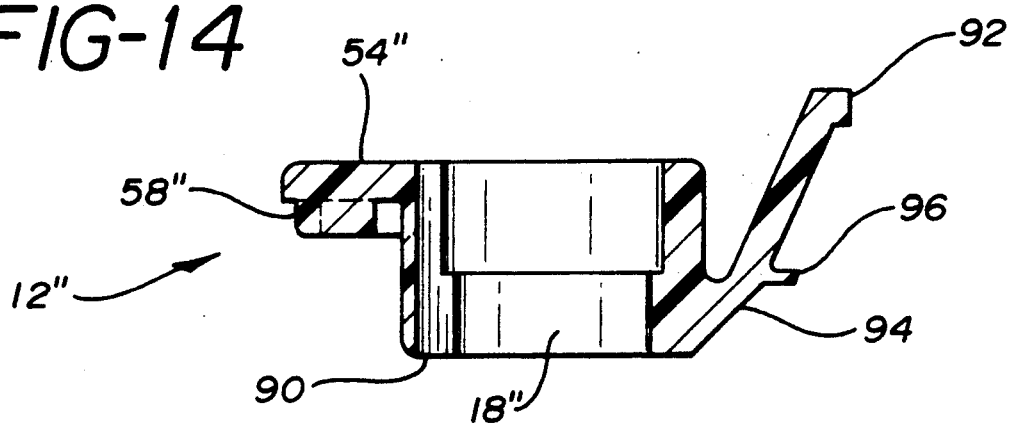
FIG. 14 is a cross-sectional view of the bearing insert of FIG. 13 along the lines 14—14.
Figure 15:
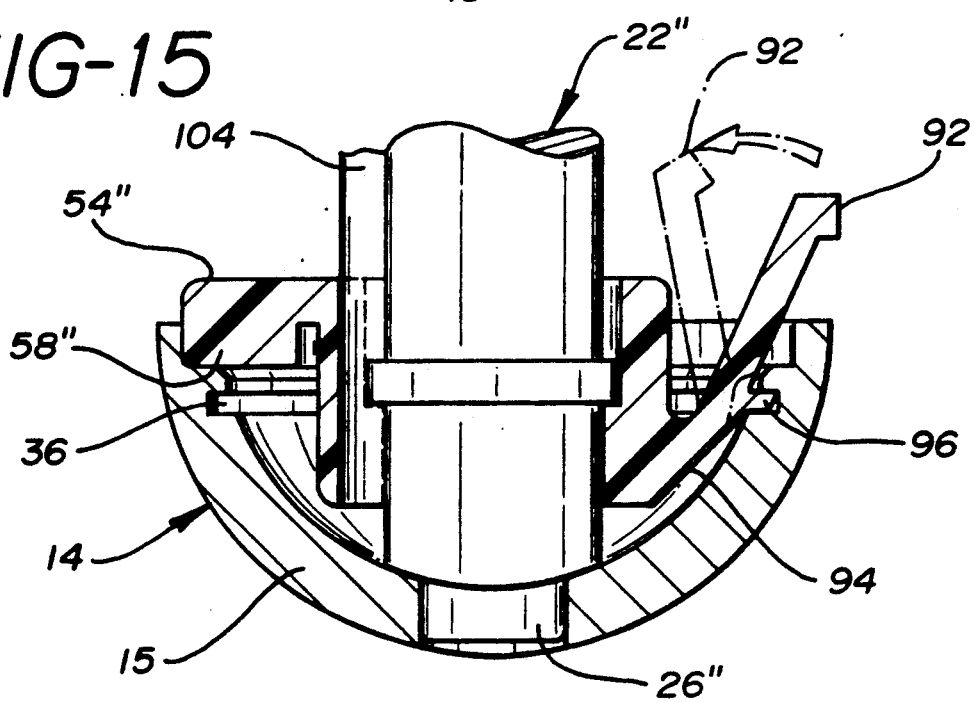
FIG. 15 is a cross-sectional view of the alternate insert mounted on the lower end of a positioning rod and coupled to the acetabular cup shell.

Referring to FIGS. 13-15, there is shown yet another embodiment of an insert of the present invention generally denoted as 12". Insert 12", preferably made of a resilient plastic, includes a bore 18" with a keyway 58", a pair of spring elements 42", two extension plates 54", a key element 58" extending from an underside 60" of one extension plate 54". These elements function similarly in all respects to those described above for inserts 12 and 12'. Insert 12" differs from inserts 12, 12' in that spring elements 42" are molded to the leading end 90 of the insert. End 90 is the end of the insert and is adapted to be received within shell 15.

Spring element 42" has a free end 92 extending radially outwardly of insert 12" which extends beyond the open end 38 of shell 15. Spring element 42" includes a shoulder 94 and a flange 96 which is adapted to be received radially outwardly extending within recess or circumferential groove 36 on the inner surface 32 of shell 15.

Insert 12" is normally preassembled to acetabular cup 14 via the engagement of flange 96 in recess 36. The resiliency of plastic insert 12" is such that end 92 of spring element 42" may be deformed radially inwardly by finger pressure and thereby disengage flange 96 from recess 36. This permits the removal of the insert 12"/positioning rod 22 assembly from the cup 14 after its impaction in the acetabulum.

In the embodiment of FIGS. 13-15 a keyway 98 is formed on the inner bore 18" which engages a complimentary key 104 on rod 22".

Figure 16:
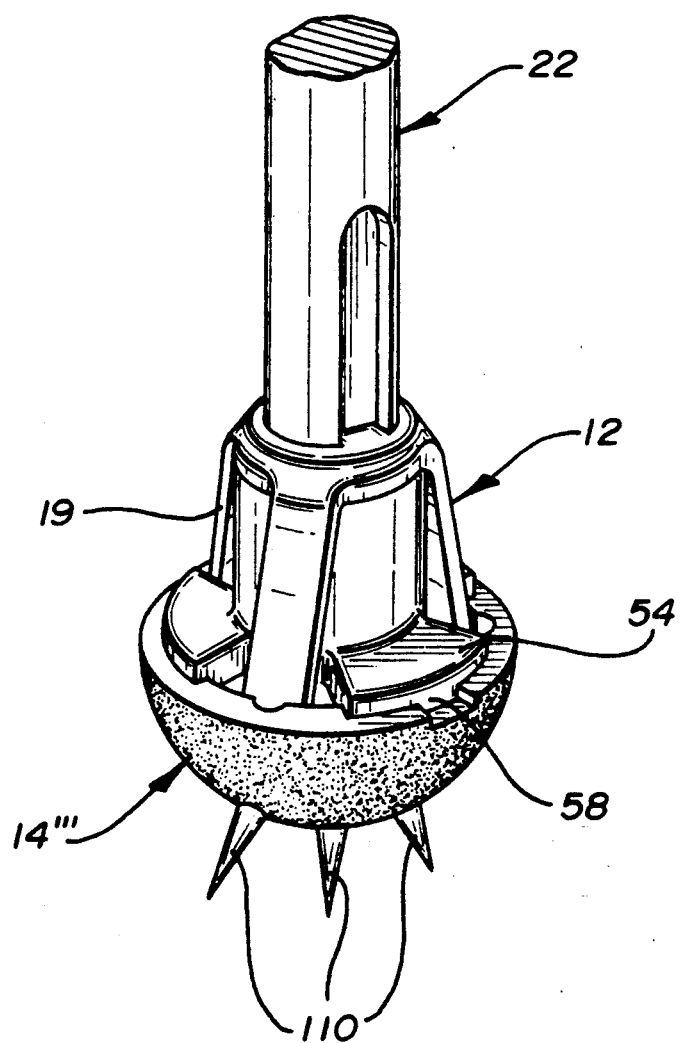
FIG. 16 is an isometric view of an alternate acetublar cup that may be used with the insert of the present invention.

While the acetabular cup shell 12 of the present invention contemplates the use of bone screws which extend through apertures 34 therein, shell 12 can also have spikes extending outwardly from outer surface 30 thereof for being driven into the bone and securing shell 12 thereto. Such spikes denoted as 110 in FIG. 16 are similar to those shown in U.S. Pat. No. 3,808,606 and are well known in the orthopaedic art.

While several examples of the present invention have been described, it is obvious that many changes and modifications may be made thereunto, without departing from the spirit and scope of the invention.

We claim:

1. An acetabular cup comprising:
   an insert having a body including a central bore for receiving a positioning rod:
   a key element formed on said bore adapted to engage a keyway on said positioning rod to align said positioning rod, said insert having a locating element formed on an outer surface of said body and a spring element extending radially outwardly from said body;
   a generally hemispherical shell member coupled to said insert and having an outer surface for engaging the acetabulum and an inner surface including means for engaging said spring element for releasably coupling said insert on said shell, said shell having a plurality of apertures extending from said inner to said outer surface of said shell member, said shell member having a means for aligning said insert locating element at a predetermined orientation with respect to said apertures so that the coupling of said insert onto said shell and the engagement of said locating element with said means for alignment aligns said key element on said central bore thereof at a predetermined orientation with respect to said apertures in said shell.

2. The acetabular cup as set forth in claim 1 wherein said locating element is a key element and said means for aligning said insert locating element is a complimentary keyway on said inner surface of said shell.

3. The acetabular cup as set forth in claim 1 wherein said means on said inner surface of said shell is a circumferential groove formed on said inner surface.

4. The acetabular cup as set forth in claim 3 wherein said spring element has at least two resilient arms connected to said insert body and extending radially outwardly therefrom, said arms having a free end including a flange for resiliently engaging said groove, said free ends spaced a sufficient distance from said body to permit resilient deformation of said arms towards said body a distance sufficient to disengage said flange from said groove.

5. An insert for a prosthetic acetabular cup shell of the type having a generally hemispherical shape with an open end and a recess on an inner surface thereof adjacent the open end, said insert comprising:
   a body having a central longitudinal bore therethrough aligned with the central axis of said hemispherical shell, said bore having a key element formed thereon, said body having a first end adapted to be received within said acetabular cup shell and a second end extending outwardly of the open end thereof, a spring element connected to said body at the first end thereof and having a free end spaced radially outwardly of said second end of said body, said free end of said spring element having a means for engaging the recess on the inner surface of the acetabular cup shell for retaining said insert within said cup.

6. The insert as set forth in claim 5 wherein said body includes an alignment element formed on an outer surface of said body for engaging the acetabular cup shell at a predetermined position thereon.

7. The insert as set forth in claim 5 wherein said alignment element is a key element formed on the first end of said body.

8. The insert as set forth in claim 7 wherein said means for engaging said recess is a flange extending radially outwardly of said spring element.

9. The insert as set forth in claim 5 wherein said free end of said spring element is radially spaced from said body a distance sufficient to permit deflection of said free end of said spring element toward said body and disengaging said means for engaging the recess from the recess on the inner surface of the acetabular cup shell.

10. An acetabular cup of the type having an outer shell including a plurality of apertures therethrough comprising:

an insert having a body including a central bore for receiving a positioning rod;

an alignment element formed on said central bore for aligning said positioning rod with respect to said insert, said insert having a locating element formed on an outer surface of said body and a means for releasably engaging the outer shell;

said outer shell having an outer surface for engaging the acetabulum and an inner surface including means for capturing said means on said insert for releasably engaging the outer shell, said outer shell including means for aligning said insert locating element at a predetermined orientation with respect to the apertures in the outer shell so that upon engagement of said insert with said outer shell and the engagement of said locating element with said means for aligning, said alignment element on said central bore is aligned at a predetermined orientation with respect to said apertures.

11. The acetabular cup as set forth in claim 10 wherein said alignment element is a key element extending longitudinally along said central bore.

12. The acetabular cup as set forth in claim 10 wherein said locating element is a key element formed on an end of said body engaging said inner surface of said outer shell.

13. The acetabular cup as set forth in claim 12 wherein said means for aligning said insert is a recess formed on an end surface connecting said inner and outer surfaces at an open end of said outer shell.

14. The acetabular cup as set forth in claim 13 wherein said means for capturing said means for releasably engaging the outer shell is a circumferential groove formed on said inner surface.

15. The acetabular cup as set forth in claim 14 wherein said spring element has a resilient arm connected to said insert body and extending radially outwardly therefrom, said arm having a free end including a flange for resiliently engaging said groove, said free end spaced a sufficient distance from said body to permit resilient deformation of said arm towards said body a distance sufficient to disengage said flange from said groove.

16. The acetabular cup as set forth in claim 10 wherein said means for releasably engaging said outer shell is a spring element resiliently coupled to said body.

17. An acetabular cup comprising:

an insert having a body including a central bore for receiving a positioning rod:

a key element formed on said bore adapted to engage a keyway on said positioning rod to align said positioning rod, said insert having a locating element formed on an outer surface of said body and a spring element extending radially outwardly from said body;

a generally hemispherical shell member coupled to said insert and having an outer surface for engaging the acetabulum and an inner surface including means for engaging said spring element for releasably coupling said insert on said shell, said shell having a plurality of spikes extending outwardly of said outer surface of said shell member, said shell member having a means for aligning said insert locating element at a predetermined orientation with respect to said spikes so that the coupling of said insert onto said shell and the engagement of said locating element with said means for alignment aligns said key element on said central bore thereof at a predetermined orientation with respect to said spikes in said shell.

18. The acetabular cup as set forth in claim 17 wherein said locating element is a key element and said means for aligning said insert locating element is a complimentary keyway on said inner surface of said shell.

19. The acetabular cup as set. forth in claim 17 wherein said means on said inner surface of said shell is a circumferential groove formed on said inner surface.

20. The acetabular cup as set forth in claim 19 wherein said spring element has at least two resilient arms connected to said insert body and extending radially outwardly therefrom, said arms having a free end including a flange for resiliently engaging said groove, said free ends spaced a sufficient distance from said body to permit resilient deformation of said arms towards said body a distance sufficient to disengage said flange from said groove.

* * * * *